United States Patent [19]

Mehra

[11] Patent Number: 4,578,094
[45] Date of Patent: Mar. 25, 1986

[54] HYDROCARBON SEPARATION WITH A PHYSICAL SOLVENT

[76] Inventor: Yuv R. Mehra, P.O. Box 3986, Odessa, Tex. 79760

[21] Appl. No.: 637,210

[22] Filed: Aug. 3, 1984

Related U.S. Application Data

[63] Continuation-in-part of Ser. No. 532,005, Sep. 13, 1983, which is a continuation-in-part of Ser. No. 507,564, Jun. 24, 1983, which is a continuation-in-part of Ser. No. 374,270, May 3, 1982, Pat. No. 4,421,535.

[51] Int. Cl.$^4$ ............................................. F25J 3/02
[52] U.S. Cl. ....................................... 62/17; 55/68; 55/73
[58] Field of Search ................... 62/20, 17; 55/68, 73; 585/800, 860, 862, 864, 866; 208/334, 332, 333, 325–327, 330, 331, 361

[56] References Cited

U.S. PATENT DOCUMENTS

| | | | |
|---|---|---|---|
| 2,139,375 | 12/1938 | Mills et al. | 23/2 |
| 2,290,957 | 7/1942 | Hackmuth | 196/8 |
| 2,649,166 | 8/1953 | Porter et al. | 183/115 |
| 2,745,889 | 5/1956 | Johnston et al. | 260/677 |
| 2,849,371 | 8/1958 | Gilmore | 196/2 |
| 3,287,262 | 11/1966 | Jones | 208/341 |
| 3,362,133 | 1/1968 | Kutsher et al. | 55/44 |
| 3,594,985 | 7/1971 | Ameen et al. | 55/73 |
| 3,664,091 | 5/1972 | Hegwer | 55/29 |
| 3,737,392 | 6/1973 | Ameen et al. | 252/364 |
| 3,837,143 | 9/1974 | Sutherland et al. | 55/32 |
| 3,877,893 | 4/1975 | Sweny et al. | 55/32 |
| 4,235,613 | 11/1980 | Castoe et al. | 62/17 |
| 4,276,057 | 6/1981 | Becker et al. | 50/40 |
| 4,302,220 | 11/1981 | Volkamer et al. | 55/32 |
| 4,318,715 | 3/1982 | Chou | 55/44 |
| 4,345,918 | 8/1982 | Meissner | 55/38 |

OTHER PUBLICATIONS

Sweny, John W., "High CO$_2$–High H$_2$S Removal with Selexol Solvent," Mar. 17–19, 1980, 59th Annual GPA Convention, Houston, Texas.

*Primary Examiner*—Frank Sever
*Attorney, Agent, or Firm*—Depaoli & O'Brien

[57] ABSTRACT

A stream of natural gas, which is rich in C$_5$+ hydrocarbons and may be wet or dry or sweet or sour, is extracted in two stages with a physical solvent. In the first stage, a major portion of the solvent, containing up to an equilibrium amount of C$_5$+ hydrocarbons, removes substantially all of the water and the C$_2$+ hydrocarbons. In the second stage, the partially stripped natural gas is countercurrently extracted with a lean-and-dry minor portion of the solvent which contains less than 1% by weight of water and less than 1% by volume of hydrocarbons. The residue natural gas, which is then sent to a pipeline, contains less than 7 pounds of water per million standard cubic feet. The rich solvent is flashed to atmospheric pressure in at least two stages, forming a methane-rich vapor portion which is suitably recycled to the first extraction, a methane-poor vapor portion, and a flashed solvent containing up to equilibrium amounts of C$_5$+ hydrocarbons. The methane-poor vapor portion is compressed, cooled, and condensed to form a liquid stream which is selectively stripped of C$_1$, C$_1$+C$_2$, C$_1$+C$_2$+C$_3$ or C$_1$+C$_2$+C$_3$+C$_4$ to form a liquid hydrocarbon product of selected composition based on market economics. A slipstream of the flashed solvent, containing the amount of water picked up from the natural gas stream and amounting to less than 25% by weight of the flashed solvent, is all that needs to be regenerated to form the lean-and-dry minor portion.

22 Claims, 1 Drawing Figure

HYDROCARBON SEPARATION WITH A PHYSICAL SOLVENT

RELATED APPLICATIONS

This is a continuation-in-part of co-pending application Ser. No. 532,005, filed Sept. 13, 1983, of Yuv R. Mehra entitled "Process for Flexibly Rejecting Selected Components Obtained from Natural Gas Streams", which is a continuation-in-part of co-pending application Ser. No. 507,564, filed June 24, 1983, of Yuv R. Mehra, entitled "Process for Recovery of Natural Gas Liquids from Natural Gas Streams with Physical Solvents", which is a continuation-in-part of Ser. No. 374,270, filed May 3, 1982, and now U.S. Pat. No. 4,421,535 of Yuv R. Mehra, issued Dec. 20, 1983, and entitled "Process for Recovery of Natural Gas Liquids Frpm A Sweetened Natural Gas Stream".

BACKGROUND OF THE INVENTION

1. Field of the Invention

This invention relates to the treatment of hydrocarbons and more specifically relates to separating and recovering ethane and higher boiling hydrocarbons with a physical solvent from a natural gas stream which is sour or which has been sweetened by removal of acidic components, such as $CO_2$, $H_2S$, RSH, and RSSR, and especially relates to economical separation of $C_5+$ hydrocarbons from the physical solvent.

2. Review of the Prior Art

Numerous processes have been used to extract liquids from natural gas streams. These processes include oil absorption, refrigerated oil absorption, simple refrigeration, cascaded refrigeration, Joule-Thompson expansion, and cryogenic turbo-expansion. Typical recoveries for these processes are given in Table I.

TABLE 1

COMPARISON OF TYPICAL LIQUID RECOVERIES

| EXTRACTION PROCESS | ETHANE (%) | PROPANE (%) | BUTANES (%) | GASOLINE (%) |
|---|---|---|---|---|
| ABSORPTION | 4 | 24 | 75 | 87 |
| REFRIGERATED ABSORPTION | 15 | 65 | 90 | 95 |
| SIMPLE REFRIGERATION | 35 | 80 | 93 | 97 |
| CASCADED REFRIGERATION | 70 | 96 | 99 | 100 |
| JOULE-THOMPSON EXPANSION | 75 | 96 | 99 | 100 |
| TURBO-EXPANDER | 85 | 97 | 100 | 100 |

In summary, the oil absorption, refrigerated oil absorption, simple refrigeration, and cascaded refrigeration processes operate at the pipeline pressures, without letting down the gas pressure, but the recovery of desirable liquids (ethane plus heavier components) is quite poor, with the exception of the cascaded refrigeration process which has extremely high operating costs but achieves good ethane and propane recoveries. The Joule-Thompson and cryogenic expander processes achieve high ethane recoveries by letting down the pressure of the entire inlet gas, which is primarily methane (typically 80-85%), but recompression of most of the inlet gas is quite expensive.

In all of the above processes, the ethane plus heavier components are recovered in a specific configuration determined by their composition in the raw natural gas stream and equilibrium at the key operating conditions of pressure and temperature within the process.

Under poor economic conditions when ethane price as petrochemical feedstock is less than its equivalent fuel price and when the propane price for feedstock usage is attractive, the operator of a natural gas liquid extraction plant is limited as to operating choice because he is unable to minimize ethane recovery and maximize propane recovery in response to market conditions.

The refrigeration process which typically recovers 80% of the propane also typically requires the recovery of 35% of the ethane. In order to boost propane recovery to the 95+% level, cascaded refrigeration, Joule-Thompson, or cryogenic turbo-expander processes would have to be used while simultaneously boosting the ethane recovery to 70+% at a considerably larger capital investment.

Extraction processes are available that employ liquids other than hydrocarbon oils for removal of acidic components, including $H_2S$ and $CO_2$, and water. These liquids comprise most physical solvents, such as propylene carbonate, N-methyl pyrrolidone, glycerol triacetate, polyethyleneglycol dimethyl ether, triethylolamine, tributyl phosphate, and gamma butyrolactone.

U.S. Pat. No. 3,594,985 describes a process for removing acid gas from a sour natural gas by countercurrently contacting the natural gas with a mixture of dimethyl ethers of polyethylene glycols containing less than 1 weight percent acid gas within two absorption zones operated in series. The rich solvent is flashed to a low pressure, and about 20-95 weight percent of the solvent is passed from the low-pressure flash tank through a cooler to the first absorption zone, with the residual portion of the solvent being sent to a stripping zone wherein essentially all of the hydrogen sulfide is removed. The well-stripped solvent containing essentially no hydrogen sulfide is then fed to the top of the first absorption zone and is next fed to the top of the second absorption zone.

As presented at the 50th Annual Gas Processors Association Convention, Mar. 17-19, 1980, in a paper entitled "High $CO_2$—High $H_2S$ Removal with SELEXOL Solvent" by John W. Sweny, the relative solubility in dimethyl ether of polyethylene glycol (DMPEG) of $CO_2$ over methane is 15.0 while that of propane over methane is 15.3. The relative solubility in DMPEG of $H_2S$ over methane is 134 versus 165 for hexane over methane in DMPEG. The relative solubilities in DMPEG of iso and normal butanes and iso and normal pentanes are in between those of propane and $H_2S$. These data indicate that if $CO_2$ and $H_2S$ are present in a natural gas stream which contains the $C_2+$ heavier hydrocarbons that are desirable for petrochemical industry feedstocks, substantial quantities of $C_2+$ hydrocarbons will be lost with $CO_2$ and $H_2S$ vent streams when the natural gas stream is treated with DMPEG.

There has nevertheless existed a need for a process wherein $C_2+$ hydrocarbons and water could be simultaneously removed to any selected degree without also extracting hydrocarbons of lower molecular weight, such as methane. There has additionally existed a need for a process wherein any natural gas, from very sour to entirely sweet, could be handled by the same equipment while simultaneously dehydrating the gas and recovering the heavier hydrocarbons.

These needs have been met by the process which is described in U.S. Pat. No. 4,421,535 and in the parent applications, Ser. Nos. 06/507,564 and 06/532,005, and which is incorporated herein by reference. This process uses physical solvents for extracting ethane and heavier hydrocarbon components and water, if present, from a natural gas stream at any desired ethane recovery from 2% to 98% while recovering 99+% of propane and all heavier hydrocarbons. It can also achieve any desired propane recovery from 2% to 99+% while recovering 99+% of butanes and all heavier hydrocarbons without recovering more than 2% of ethane. The inlet gas pressure can range from 300 psig to 1300 psig and from an ambient temperature of 75° F. to 120° F.

This process produces a liquid hydrocarbon product having a composition which is selectively versatile rather than fixed, as in prior art processes. In consequence, the composition of its hydrocarbon product can be readily adjusted in accordance with market conditions so that profitability of the absorption operation can be maximized at all times and on short notice.

The extraction and recovery process described in U.S. Pat. No. 4,421,535, in Ser. No. 507,564, and in Ser. No. 532,005 uses excessive energy when simultaneously dehydrating residue gas to less than 7 pounds $H_2O$ per million standard cubic feet and releasing $C_5+$ hydrocarbons in the atmospheric flashing stage. It is true that when the natural gas contains relatively low quantities of $C_5+$ components, there is no need for a vacuum flash; atmospheric flashes are satisfactory, and the process works well. However, if the $C_5+$ hydrocarbons are present in significant quantities in the natural gas, such significant quantities being defined as any amount greater than 0.2 mol or volume percent, the solvent cannot release these hydrocarbons without flashing to a subatmospheric pressure and thus the $C_5+$ hydrocarbons continue to build up in the solvent until an equilibrium is reached on the order of 14–15% of hydrocarbons by volume in the solvent stream if the solvent regenerator is bypassed to conserve energy consumption.

The presence of these $C_5+$ hydrocarbons at the top of the extraction tower tends to limit absorption of $C_5+$ hydrocarbons from the inlet natural gas stream because the $C_5+$ hydrocarbons present in lean solvent reach an equilibrium with the residue natural gas stream and therefore tend to remain in the residue natural gas stream. In other words, the need to maximize recovery of heavier hydrocarbons requires the lean solvent to contain no more than about one volume percent of $C_5+$ hydrocarbons and preferably less than 0.5% by volume of $C_5+$ hydrocarbons. Furthermore, flashing to sub-atmospheric pressure is expensive, and when the $C_5+$ hydrocarbons content in the inlet gas stream is greater than 0.2 mol percent, this flashing stage does not produce a $C_5+$ hydrocarbon-free solvent for recycle to the extractor. There is consequently a need for a more economical method for removing these $C_5+$ hydrocarbons from the near atmospheric pressure solvent.

Another characteristic of the process described in U.S. Pat. No. 4,421,535 and in Ser. Nos. 507,564 and 532,005 is that natural gas in its normally saturated state is stripped of an appreciable amount of water in the extraction stage. This water, carried by the rich solvent through the one or more flashing stages, is then removed by regenerating the entire volume of solvent in a regenerating stage which requires heating the solvent to a temperature of about 300° F. and subsequently cooling it to ambient temperature. Such heating and cooling is also quite expensive, so that there is a need for a less energy-consuming process for simultaneously dehydrating the natural gas stream and selectively removing its $C_2+$ hydrocarbon content.

SUMMARY OF THE INVENTION

It is accordingly an object of this invention to provide a method for separating $C_5+$ hydrocarbons and water, if present, from the solvent without heating and cooling the entire mass of the solvent stream in order to minimize use of energy.

It is another object of this invention to provide a continuous process for simultaneously extracting $C_5+$ hydrocarbons to a maximum degree along with $C_2+$ hydrocarbons from a natural gas stream with a physical solvent and then for separating the extracted $C_5+$ hydrocarbons from the solvent, with or without use of sub-atmospheric pressure flashing.

Another object is to provide a continuous process for simultaneously dehydrating a natural gas stream containing at least 0.2 mol % $C_5+$ hydrocarbons without regenerating the entire solvent stream.

In accordance with these objectives and the principles of this invention, an improved process is provided which minimizes the energy required for dehydration and removal of $C_2+$ hydrocarbons with a physical solvent after using the solvent for continuously extracting a liquid hydrocarbon product of a selected composition, which is selectively adjustable to substantially any selected degree in accordance with market conditions, from an inlet natural gas stream containing at least 0.2 mol or volume % of $C_5+$ hydrocarbons and while producing a residue natural gas stream of pipeline quality that selectively includes ethane ($C_2$), propane ($C_3$), and/or butanes ($C_4$).

This improved process comprises the following steps:

A. dividing the solvent stream into a major solvent stream and a minor solvent stream and selectively extracting the inlet natural gas stream in a first extraction stage with the major solvent stream, which is at a selected solvent flow rate per standard cubic foot of the gas stream, and in a second extraction stage with the minor solvent stream, the major solvent stream containing up to an equilibrium amount of $C_5+$ hydrocarbons and the minor solvent stream being lean with respect to $C_1+$ hydrocarbons and dry with respect to water, whereby the rich solvent stream and the residue natural gas stream are produced, this residue natural gas stream containing selected maximum amounts of $C_2+$ hydrocarbons and less than 7 pounds of water per million standard cubic feet;

B. successively flashing the rich solvent stream in a plurality of flashing stages at pressures that successively decrease to atmospheric pressure and selectively to a sub-atmospheric pressure in order to produce a plurality of successive $C_1+$ gas fractions, having successively lower methane contents, and liquid mixtures of the solvent and hydrocarbons having successively lower methane contents, the flashing pressure of the successive flashing stages being varied in order to adjust the compositions of the successive gas fractions and of the successive liquid mixtures; and C. regenerating a slipstream of the liquid mixture from the atmospheric pressure stage or selectively from the sub-atmospheric pressure stage, if utilized in step B above, in order to produce the minor solvent stream for the second extraction stage of step A, while recycling the remainder of the liquid mixture as major solvent stream to the first extraction stage of step A.

Preferably, the lean-and-dry minor solvent stream contains less than 1% by weight of water and less than 1% by volume of hydrocarbons. The minor solvent stream passes countercurrently to the natural gas stream through the second extraction stage and then may enter the first extraction stage, wherein it combines with the major solvent stream, or it may pass directly to the regeneration stage of step C as the slipstream.

At least the first of the successive $C_1+$ gas fractions is recycled to the first extraction stage in order to extract maximum quantities of the $C_2+$ hydrocarbons into the rich solvent stream. The remainder of the successive $C_1+$ gas fractions is compressed, condensed, and selectively stripped of $C_1$, $C_1+C_2$, $C_1+C_2+C_3$, or $C_1+C_2+C_3+C_4$, which are selectively recycled to the first extraction stage or are combined with the residue natural gas stream leaving the second extraction stage, producing a residue natural gas of selected composition and a $C_2+$ liquid product of selected composition.

The slipstream sent to the solvent regenerating operation produces a vapor stream which is condensed and collected in a separator from which waste water is removed. Water is also removed in a reflux stream which is sent back to the regenerator. Water is effectively used as reflux in the regenerating step in order to prevent solvent from leaving with the waste water. A hydrocarbon stream is additionally removed from the separator and combined with the flash vapors from the atmospheric flashing stage for compressing and condensing and then stripping or is sent directly to the stripping or is combined with the $C_2+$ liquid product.

The regenerated solvent slipstream contains less than 1% by weight of water and less than 1% by volume of $C_2+$ hydrocarbons. It is sent directly to the second extraction stage as the minor solvent stream where it establishes an equilibrium with the residue natural gas leaving the stage so that the residue natural gas is selectively lean with respect to $C_2+$ hydrocarbons and is as dehydrated as is economically desired.

As is disclosed in the parent applications, the capability of selectively adjusting the composition of the $C_2+$ liquid product and of the residue natural gas stream to substantially any selected degree with the process of this invention and in accordance with market conditions is obtained by utilizing at least one and preferably all of the following operational procedures:

A. selectively varying the flow rates of the major and minor solvent streams with respect to the flow rate of the natural gas stream in both extraction stages in order to adjust the composition of the residue gas stream relative to selected $C_2+$ components and its water content thereof;

B. selectively varying the flashing pressures of the successive flashing stages in order to adjust the compositions of the successive $C_1+$ gas fractions and the successive liquid mixtures relative to selected $C_2+$ components thereof;

C. recycling at least the first of these successive $C_1+$ gas fractions to the first extraction stage in order to extract maximum quantities of the ethane and heavier hydrocarbons; and D. stripping selected consecutive lowest molecular weight hydrocarbons from at least the last of the successive $C_1+$ gas fractions plus, selectively, the hydrocarbons from the separator by: (1) selectively varying the pressure of the stripping, and (2) selectively varying the bottoms temperature of the stripping.

If the natural gas stream is sour, it is preferred that it be sweetened by contact with an acid-absorbing solvent, such as an amine, before the extraction process of this invention is utilized. However, if an amine pretreating step is not suitable, the sour natural gas stream can be treated according to the instant process by maintaining the acidic components in liquid-phase solution or in vapor-phase contact, respectively, with the heavier hydrocarbon components until the solution or mixture, as a liquid, can be contacted by an acid-absorbing solvent. Because such post-absorption sweetening is done in liquid phase, the capital cost for equipment is relatively low.

The amount of the slipstream that is removed and sent to the regenerating step is always less than 25% of the total amount of solvent being circulated through the process and is always sufficient to remove the amount of water and the remaining amount of $C_5+$ hydrocarbons entering with the inlet natural gas stream. Depending upon the composition and water content of the natural gas stream, the amount of water or the amount of $C_5+$ hydrocarbons may be the limiting factor. The amount of water in the rich solvent is also never allowed to become so high that it interferes with absorption of $C_5+$ hydrocarbons, i.e., no more than 2 mol percent.

The invention may also be described as an improvement in a continuous process for extracting and selectively recovering $C_2+$ hydrocarbons to substantially any selected degree from an inlet natural gas stream, containing at least 0.2 mol or volume percent of $C_5+$ hydrocarbons, at pipeline pressures by the following steps: (a) countercurrently extracting the inlet natural gas stream with a lean solvent stream in an extraction stage to produce a residue natural gas stream and a rich solvent stream, (b) flashing the rich solvent stream to approximately atmospheric pressure to produce flashed gases and a flashed solvent stream containing $C_5+$ hydrocarbons, (c) flashing the flashed solvent stream at below atmospheric pressure to produce the $C_5+$ hydrocarbons stream and the lean solvent stream, (d) regenerating the entire lean-and-wet solvent stream to remove water and a trace of hydrocarbons; (e) recycling a portion of the flashed gases to the extraction step, (f) condensing the remaining portion of the flashed gases, after combination with the $C_5+$ hydrocarbons stream, to produce a hydrocarbon liquid, and (g) stripping selected amounts of $C_1$-$C_4$ hydrocarbons from the hydrocarbon liquid to produce a liquid product of selected $C_2+$ hydrocarbons, wherein:

(1) failure to remove said $C_5+$ hydrocarbons according to step (c) limits absorption of $C_5+$ hydrocarbons from the inlet natural gas stream in step (a), (2) removal of hydrocarbons according to step (c) necessitates excessive energy consumption, and (3) regenerating all of the lean-and-wet solvent stream according to step (d) requires additional energy consumption.

The invention may accordingly be described as the improvement comprising the following steps:

A. replacing step (d) with the following steps:
   (1) dividing the flashed solvent stream of step (b) or step (c) into a major solvent stream and a slipstream, the major solvent stream containing an equilibrium amount of $C_5+$ hydrocarbons;

(2) regenerating the slipstream to a water content of less than 1% of water by weight and a hydrocarbon content of less than 1% of $C_2+$ hydrocarbons by volume to form a lean-and-dry minor solvent stream; and B. replacing step (a) with the following steps:
  (1) countercurrently extracting $C_2+$ hydrocarbons and water from the inlet natural gas stream with the major solvent stream at a selected solvent flow rate per standard cubic feet to produce a partially stripped and dry natural gas stream and a major portion of the rich solvent stream in a first extraction stage, and
  (2) countercurrently extracting the partially stripped natural gas stream with the lean and dry minor solvent stream to produce the residue natural gas stream containing less than 7 pounds of water per million standard cubic feet and a minor enriched solvent stream containing the remaining $C_5+$ hydrocarbons.

Moreover, the liquid mixture from the atmospheric pressure stage may be selectively flashed at below atmospheric pressure to produce the $C_5+$ hydrocarbons as flashed gases, which are sent to the stripping of step (g), and a selectively lean and wet solvent stream for the dividing of step A.

Below-atmospheric pressure flashing is selectively employed and the pressure in the below-atmospheric pressure stage is selected in order to minimize total energy consumption of the improved process, by balancing the amount of the minor solvent stream and the energy required for the regenerating thereof according to step B against the energy required for the below-atmospheric pressure stage.

It is characteristic of the parent processes that the regenerator is used primarily to remove water from all of the solvent by distillation, with water being refluxed from the separator to the column in order to keep the solvent from reaching the top of the column and with trace amounts of hydrocarbons also being removed from the separator and sent to one of the flashing stages.

It is characteristic of this invention, however, that the regenerator is used to remove $C_5+$ hydrocarbons in substantial quantity from a minor portion (up to 25% and preferably much less, such as 10%) of the total solvent. The separator is similarly used to separate the usually substantial quantity of $C_5+$ hydrocarbons from the generally substantial quantity of water, both quantities having been distilled from the slipstream or minor portion of solvent discharged as bottoms from the terminal flashing stage. If the inlet natural gas stream is dry, however, water must nevertheless be introduced to the separator and returned to the column as a constantly recycling quantity in order to keep the solvent from reaching the top of the column. The separate $C_5+$ stream is then sent to the stripper for removing selected $C_1$-$C_4$ hydrocarbons or is discharged as a part of the liquid hydrocarbon product.

BRIEF DESCRIPTION OF THE DRAWING

The invention may be more readily understood by referring to the drawing which diagrammatically illustrates a preferred embodiment for treating sweet natural gas for removal of water and hydrocarbons heavier than methane from a natural gas stream.

DESCRIPTION OF THE PREFERRED EMBODIMENTS

Figure 1:
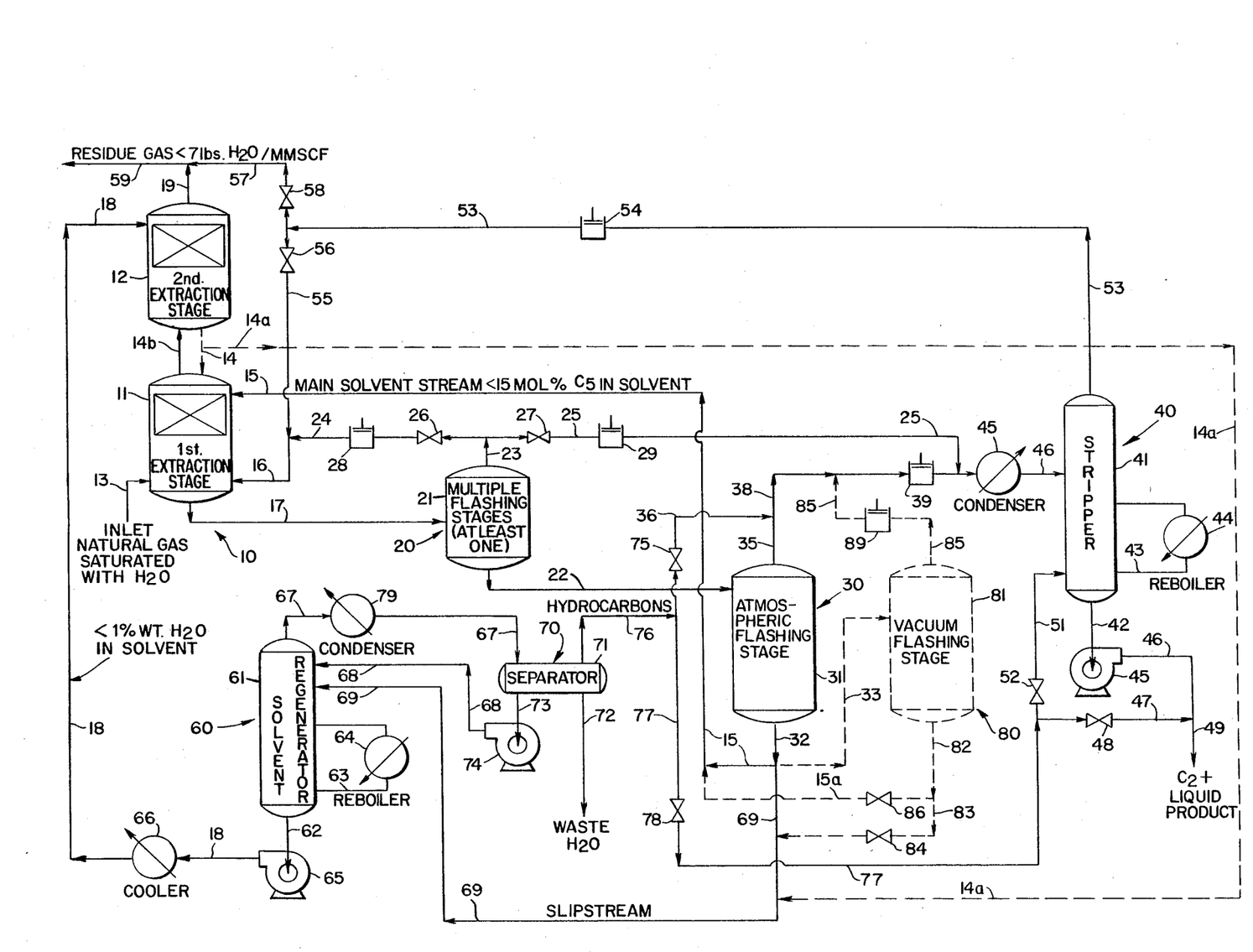
The FIGURE is an overall schematic flow sheet illustrating the utilization of the flexible process of this invention for selectively recovering $C_2+$, $C_3+$, $C_4+$, or $C_5+$ hydrocarbons from a natural gas stream, having any water content up to saturation, while minimizing the expenditures of energy for separating $C_5+$ hydrocarbons from the rich solvent and for regenerating the solvent sufficiently to dehydrate the residue natural gas stream to less than 7 pounds of water per million standard cubic feet.

The process shown schematically in the FIGURE comprises an extraction unit 10, at least one flashing stage 20, an atmospheric flashing stage 30, a stripper 40, a solvent regenerator 60, and a separator 70. Extraction unit 10 comprises two stages, a first extraction stage and a second extraction stage, which may be combined in a single vessel but which is shown in the drawing as two vessels for illustrating the function, shown as being a first vessel 11 and a second vessel 12.

Referring to the FIGURE, a natural gas stream, normally saturated with water but in some circumstances completely dry, enters the bottom of vessel 11 through line 13 while a stream of flashed gases, mostly $C_1$ to $C_4$, also enters the bottom of vessel 11 in line 16. A main solvent stream, containing up to 15 mol % $C_5+$ hydrocarbons, enters the top of vessel 11 in line 15 so that the solvent flows downwardly and countercurrently to the upwardly flowing natural gas. A stream of rich solvent in line 17 leaves the bottom of vessel 11.

The partially stripped natural gas leaves the top of vessel 11 through line 14b and enters the bottom of the second extraction stage in vessel 12. A stream of lean-and-dry solvent, containing less than one weight percent of water and less than one volume percent of $C_5+$ hydrocarbons, enters the top of vessel 12 through line 18 and flows downwardly, countercurrently to the upwardly flowing natural gas, until it departs through line 14, selectively entering the top of vessel 11 or partially or entirely bypassing vessel 11 through line 14a to join stream 69 and enter solvent regenerator 60. The residue natural gas, in equilibrium with the lean-and-dry solvent in line 18, leaves vessel 12 through line 19.

The rich solvent in line 17 leaves the bottom of vessel 11 and flows to at least one flashing stage 20, exemplified by vessel 21 in which the rich solvent is flashed at an intermediate pressure, releasing flashed gases which leave the top of vessel 21 through line 23 and return to the first extraction stage through line 24, valve 26, and compressor 28 or pass through line 25, valve 27, and compressor 29 for further treatment in a stripper unit 40.

The partially leaned solvent leaves vessel 21 through line 22 as feed for an atmospheric flashing stage 30, comprising a vessel 31 in which the solvent is reduced in pressure to approximately atmospheric pressure to produce lower molecular weight hydrocarbons which are flashed to the upper portion of vessel 31 and leave as a vapor stream in line 35. Additional flashed gases in line 36, controlled by valve 75, are combined with this vapor stream and travel through line 38, are compressed by compressor 39, and are joined by the vapor in line 25 to form a combination of three streams (lines 35, 36, 25) which enters line 46 to become a liquid in condenser 45 as feed for stripper unit 40.

Stripper unit 40 may be operated as a demethanizer, a de-ethanizer, a depropanizer, or a debutanizer, respectively removing $C_1$, $C_1+C_2$, $C_1+C_2+C_3$, or $C_1+C_2+C_3+C_4$ overhead. Stripper unit 40 comprises a stripping vessel 41, a recirculating line 43, and a reboiler 44. The $C_1$-$C_4$ gases are removed from the incoming liquid in vessel 41 and passed through line 53 and compressor 54 to selectively alternate destinations. One destination is through line 55 and valve 56, to join line 24 and enter line 16, or through line 57 and valve 58, to join line 19 and enter line 59, whereby the $C_1$-$C_4$ gases become a part of the residue natural gas.

The stripped liquid leaves vessel 41 through line 42, pump 45, and line 46 until joined by the additional hydrocarbons in line 47 with a valve 48 to form a combined hydrocarbon liquid product which is discharged through line 49.

A stream of solvent, which has been stripped of $C_1+$ hydrocarbons and is approximately saturated with $C_5+$ hydrocarbons, leaves vessel 31 through line 32. After removal of a slipstream thereof through line 69, the remainder flows through line 15 to enter the top of vessel 11 of the first extraction stage.

The slipstream in line 69 enters vessel 61 of solvent regenerator 60, wherein circulation through line 63 and reboiler 64 distills water and hydrocarbons from the solvent which leave at the top thereof through line 67 and condenser 79 to enter vessel 71 of separator unit 70. A stream of waste water leaves vessel 71 through line 72, and a stream of reflux, primarily composed of water, passes through line 73 and pump 74 to return to the top of vessel 61 through line 68.

A stream of hydrocarbons leaves vessel 71 through line 76 to pass through line 36 and valve 75 and join the vapors in line 35 as eventual feed for stripper unit 40 or, alternatively, passes through line 77 and valve 78 and then through line 51 and valve 52 to enter vessel 41 or, alternatively, then through line 47 and valve 48 to join line 46 and form line 49, whereby the hydrocarbons removed from the solvent in solvent regenerator 60 enter vessel 41 as a liquid after combination with vapors from vessel 31, or leave vessel 71 as a liquid and as feed for vessel 41, or join the liquid products from vessel 41 to form the $C_2+$ liquid product of the process in line 49.

The lean-and-dry solvent produced by solvent regenerator 60 passes through line 62 and pump 65 to enter line 18 and cooler 66 to form the lean-and-dry minor solvent feed stream for the second extraction stage.

This process for partial regeneration of a slipstream of the flashed solvent and for extraction of the natural gas in at least two stages, the last stage using the regenerated solvent, clearly minimizes energy consumption by selectively eliminating or changing the pressure of the vacuum flashing stage and by greatly reducing the quantity of solvent which must be regenerated.

As in the process of U.S. Pat. No. 4,421,535, the flashed solvent stream in line 32 from atmospheric flashing stage 30 may be selectively sent through line 33 to vacuum flashing stage 80 where most of the remaining hydrocarbons are flashed out of the solvent. The vacuum-flashed solvent is discharged from vacuum vessel 81 through line 82 and a pump (not shown in the FIGURE) to be split into a slipstream in line 83, which is controlled by valve 84 and enters line 69, and a major stream in line 15a which is controlled by valve 86. The flashed gases, containing most of the $C_5+$ hydrocarbons in the flashed solvent stream, are discharged through line 85, are compressed by compressor 89, and enter line 38 for further compression by compressor 39 and liquefaction in condenser 45.

The criteria for selectively utilizing vacuum flashing stage 80 and for selecting a sub-atmospheric pressure therein are the amount of slipstream in line 69 and the proportionate quantity of hydrocarbon in line 76. As the operator notes increases in both quantities, while the water content of the lean and dry minor solvent stream in line 18 remains within limits, he knows that the additional regenerating costs may be reduced by activating vacuum flashing stage 80 at a selected sub-atmospheric pressure. The total energy consumption of compressor 89 and reboiler 64 determines the application of vacuum flashing unit 80 in the instant process.

EXAMPLE 1

The quantity of the slipstream is hereinafter calculated as a percentage of the total solvent stream, based on the maximum water content of the major solvent stream and utilizing data from the Example of U.S. Pat. No. 4,421,535.

A plant for selectively recovering hydrocarbons from a natural gas stream, utilizing the process of the FIGURE, is designed and put into operation to treat wet natural gas, measured as one million standard cubic feet (MMSCF) per day of dry sweetened natural gas. The water content of the inlet natural gas stream is 169 lbs $H_2O$/MMSCF, equalling 9.4 lb-mols/day of water. The inlet pressure is 625 psia and the inlet temperature is 120° F. The residue gas flowrate in stream 19 is:

$$19.02 \text{ lb-mols/hr} \times 379.49 \text{ ft}^3/\text{mol} \times 24 \text{ hrs/day} = 0.829 \text{ MMSCFD}.$$

The water specification for the residue gas in stream 19 is 7 lbs $H_2O$/MMSCFD. Therefore, the maximum permissible water content of the residue gas $= 7 \times 0.829 = 5.8$ lbs $H_2O$. The water to be removed by the solvent of streams 15, 18 in extraction stage 10 is:

$$169 - 5.8 = 163.2 \text{ lbs } H_2O$$

The maximum permissible water concentration in the lean and dry solvent of stream 18 is 2 mol % which is equivalent to:

|  | mol % |  | lbs/lb mol |  | lbs | Wgt % |
|---|---|---|---|---|---|---|
| $H_2O$ | 2 | X | 18 | = | 36 | 0.13 |
| Solvent | 98 | X | 280 | = | 27,440 | 99.87 |
|  | 100 |  |  |  | 27,476 | 100.00 |

The solvent slipstream 69 to regenerating stage 60 contains 163.2 lbs $H_2O$, equalling:

$$\frac{163.2 \times 0.9987}{0.0013} =$$

125,375 lbs/day of pure solvent in minor solvent stream 18

The flowrate of the pure solvent in stream 32 is:

$$150 \text{ lb-mols/hr} \times 24 \text{ hrs/day} \times 280 \text{ lbs/lb mol} = 1,008,000 \text{ lbs/day}.$$

On the basis of pure solvent only, the slipstream as a percentage of the total solvent is:

$$\frac{125,375}{1,008,000} \times 100 = 12.44\%$$

This split of the solvent flow represents an energy savings of about 87% since about 87% of the flashed solvent is recycled as the major solvent stream to the first extraction stage without being regenerated.

EXAMPLE 2

The following table presents a material balance around the first and second extraction stages of extraction unit 10 as shown in the FIGURE for an inlet natural gas stream, having the composition of the corresponding stream in the Example of U.S. Pat. No. 4,421,535, when contacted with a solvent stream containing 10 mol % of hydrocarbons, all of which are $C_5+$ hydrocarbons. It should be understood that streams 14b and 17 are calculated as if stream 14 from the second extraction stage is not added to solvent stream 15 within the first extraction stage but is sent directly to regenerator 60 through line 14a. Accordingly, when stream 14 is fed to the first extraction stage, streams 14b and 17 will have different compositions than those shown in the table.

| | First Extraction Stage | | | |
|---|---|---|---|---|
| Component mols/hr | Inlet Gas 13 | Inlet Solvent 16 | Discharged Solvent 15 | Gas Discharge 17 | 14b |
| Nitrogen | 2.22 | 0.11 | — | 0.11 | 2.24 |
| Methane | 88.48 | 25.54 | — | 25.76 | 90.50 |
| Ethane | 10.63 | 2.00 | — | 12.09 | 0.65 |
| Propane | 5.30 | 0.30 | — | 5.60 | 0.04 |
| Iso-Butane | 0.55 | 0.02 | — | 0.57 | 0.01 |
| N—Butane | 1.59 | 0.04 | — | 1.63 | 0.03 |
| Iso-Pentane | 0.33 | — | 2.5 | 2.83 | 0.33 |
| N—Pentane | 0.41 | — | 4.5 | 4.91 | 0.41 |
| Hexane Plus | 0.29 | — | 8.0 | 8.29 | 0.29 |
| Water | 0.39 | — | 3.0 | 3.39 | 0.02 |
| Solvent | — | — | 132.0 | 150.0 | — |
| Total | 110.19 | 28.01 | 150.0 | 215.18 | 94.52 |

| | Second Extraction Stage | | | |
|---|---|---|---|---|
| Component mols/hr | Inlet Gas 14b | Inlet Solvent 18 | Solvent Discharge 14a | Gas Discharge 19 |
| Nitrogen | 2.24 | — | 0.02 | 2.22 |
| Methane | 90.50 | — | 2.02 | 88.26 |
| Ethane | 0.65 | — | 0.11 | 0.54 |
| Propane | 0.04 | — | 0.04 | Trace |
| Iso-Butane | 0.01 | — | 0.01 | — |
| N—Butane | 0.03 | — | 0.03 | — |
| Iso-Pentane | 0.33 | — | 0.33 | — |
| N—Pentane | 0.41 | — | 0.41 | — |
| Hexane Plus | 0.29 | — | 0.29 | — |
| Water | 0.02 | — | 0.02 | — |
| Solvent | — | 18.0 | 18.0 | — |
| Total | 94.52 | 18.0 | 21.28 | 91.02 |

Because it will be readily apparent to those skilled in the art of treating natural gas that innumerable variations, modifications, amplifications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. In a continuous process for producing a liquid hydrocarbon product of a selected composition, which is selectively adjustable to substantially any selected degree in accordance with market conditions, and a residue natural gas stream of pipeline quality that selectively includes ethane ($C_2$), propane ($C_3$), and butanes ($C_4$) by extraction of an inlet natural gas stream, containing at least 0.2 mol percent of $C_5+$ hydrocarbons, with a stream of a physical solvent, an improvement which comprises:

minimizing the energy required for said process while recovering up to 100% of said $C_5+$ hydrocarbons in accordance with said market conditions by the following steps:

A. selectively extracting said inlet natural gas stream in a first extraction stage with a major solvent stream and in a second extraction stage with a minor solvent stream, said major solvent stream containing up to an equilibrium amount of $C_5+$ hydrocarbons and said minor solvent stream being lean with respect to $C_1+$ hydrocarbons, whereby a rich solvent stream and a residue natural gas stream are produced, said residue natural gas stream containing selected maximum amounts of $C_2+$ hydrocarbons in accordance with said market conditions;

B. successively flashing said rich solvent stream in a plurality of flashing stages at pressures that successively decrease to about atmospheric pressure in order to produce a plurality of successive $C_1+$ gas fractions, having successively lower methane contents, and flashed solvent streams containing said solvent and hydrocarbons having successively lower methane contents, the flashing pressures of said successive flashing stages being selectively varied in order to adjust the compositions of said successive gas fractions and of said successive flashed solvent streams;

C. dividing said physical solvent stream into said major solvent stream and a slipstream; and D. regenerating said slipstream in order to produce said minor solvent stream for said second extraction stage.

2. The improvement in the process of claim 1, wherein said minor solvent stream passes countercurrently to said natural gas stream through said second extraction stage and then enters said first extraction stage wherein it combines with said major solvent stream.

3. The improvement in the process of claim 2, wherein at least the first of said successive flashed $C_1+$ gas fractions is recycled to said first extraction stage in order to extract maximum quantities of $C_2+$ hydrocarbons into said rich solvent stream.

4. The improvement in the process of claim 3, wherein the remainder of said successive $C_1+$ gas fractions is compressed, condensed, and selectively stripped of $C_1$, $C_1+C_2$, $C_1+C_2+C_3$, or $C_1+C_2+C_3+C_4$, which are selectively recycled to said first extraction stage or are combined with said residue natural gas stream leaving said second extraction stage, thereby producing a residue natural gas of selected composition and said liquid hydrocarbon product of selected composition.

5. The improvement in the process of claim 4, wherein said regenerating in said step D of claim 1 also produces a $C_5+$ hydrocarbon stream which is selectively combined with said remainder of said $C_1+$ gas fractions, sent directly to said stripping step of said claim 6, or combined with said liquid hydrocarbon product.

6. The improvement in the process of claim 3, wherein said flow rates of said major solvent stream and said minor solvent stream are selectively varied with respect to the flow rate and composition of said inlet natural gas stream during said first extracting and said second extracting in order to adjust the composition of said rich solvent stream relative to selected components of the group consisting of ethane ($C_2$), propane ($C_3$), iso and normal butanes ($C_4$), and hydrocarbons heavier than normal butanes ($C_5+$):

A. dividing said flashed solvent stream of step (b) into a major solvent stream and a minor solvent stream, said major solvent stream containing an equilibrium amount of $C_5+$ hydrocarbons;

B. regenerating said minor solvent stream to a water content of less than 1% water by weight and a hydrocarbon content of less than 1% of $C_5+$ hydrocarbons by volume to form a lean and dry minor solvent stream; and   C. replacing said step (a) with the following steps:

(1) countercurrently extracting $C_2+$ hydrocarbons and water from said inlet natural gas stream with said major solvent stream at a selected solvent flow rate to produce a partially stripped and dry natural gas stream and a major portion of said rich solvent stream in a first extraction stage, and     (2) extracting said partially stripped natural gas stream with said lean and dry minor solvent stream to produce said residue natural gas stream, containing less than 7 pounds of water per million standard cubic feet and a selective amount of $C_2+$ hydrocarbons and a minor enriched solvent stream containing the remaining $C_5+$ hydrocarbons.

7. The improvement in the process of claim 1, wherein said minor solvent stream leaves said second extraction stage and enters said regenerating of said step D.

8. In a continuous process for extracting and selectively recovering $C_2+$ hydrocarbons to substantially any selected degree from an inlet natural gas stream, sweet or sour and containing water up to saturation, at pipeline pressures by the following steps: (a) countercurrently contacting the inlet natural gas stream with a lean-and-dry solvent stream in an extraction step to produce a residue natural gas stream and a rich solvent stream, (b) flashing said rich solvent stream to about atmospheric pressure to produce flashed gases and a flashed solvent stream containing $C_5+$ hydrocarbons, (c) flashing said flashed solvent stream to below atmospheric pressure to produce said $C_5+$ hydrocarbons and a lean-and-wet solvent stream, (d) regenerating said lean-and-wet solvent stream to remove water and a trace of hydrocarbons, (e) recycling a portion of said flashed gases of said step (b) to said extraction step, (f) condensing the remaining portion of said flashed gases, after combination with said $C_5+$ hydrocarbons, to produce a hydrocarbon liquid, and (g) stripping selected amounts and components of $C_1$-$C_4$ hydrocarbons from the hydrocarbon liquid to produce a liquid hydrocarbon product, wherein:

(1) failure to remove said $C_5+$ hydrocarbons according to said step (c) limits absorption of $C_5+$ hydrocarbons from said inlet natural gas stream in said step (a),   (2) removal of hydrocarbons according to said step (c) necessitates excessive energy consumption, and   (3) regenerating all of said lean-and-wet solvent stream according to said step (d) requires additional energy consumption, the improvement comprising:

minimizing the energy required for said process while recovering up to 100% of said $C_5+$ hydrocarbons in accordance with market conditions by the following steps:

A. dividing said flashed solvent stream from either said step (b) or said step (c) into a major solvent stream and a slipstream, said major solvent stream containing an equilibrium amount of $C_5+$ hydrocarbons;

B. regenerating said slipstream to a water content of less than 1% water by weight and a hydrocarbon content of less than 1% of $C_5+$ hydrocarbons by volume to form a lean-and-dry minor solvent stream; and   C. replacing said step (a) with the following steps:

(1) countercurrently extracting $C_2+$ hydrocarbons and water from said inlet natural gas stream with said major solvent stream at a selected solvent flow rate to produce a partially stripped-and-dry natural gas stream and a major portion of said rich solvent stream in a first extraction stage, and     (2) extracting said partially stripped-and-dry natural gas stream with said lean-and-dry minor solvent stream to produce said residue natural gas stream, containing less than 7 pounds of water per million standard cubic feet and a selective amount of $C_2+$ hydrocarbons in accordance with said market conditions, and a minor enriched solvent stream containing the remaining $C_5+$ hydrocrbons.

9. The improvement in the process of claims 1, 8 or 22, wherein said inlet natural gas stream is selected from the group consisting of:

A. natural gas saturated with water;
  B. natural gas at less than saturation with water;
  C. sour natural gas;
  D. sour natural gas which is pre-sweetened in gas phase with an aqueous amine solution;
  E. sweet natural gas; and
  F. dry natural gas.

10. The improvement in the process of claim 9, wherein said physical solvent is selective toward ethane and heavier hydrocarbon components of said inlet natural gas stream over methane such that the relative volatility of methane over ethane is at least 5.0 and the hydrocarbon loading capacity, defined as solubility of ethane in solvent, is at least 0.25 standard cubic feet of ethane per gallon of solvent.

11. The improvement in the process of claim 10, wherein said physical solvent is selected from the group consisting of dialkyl ethers of polyalkylene glycol, N-methyl pyrrollidone, dimethyl formamide, propylene carbonate, sulfolane, and glycerol triacetate.

12. The improvement in the process of claim 11, wherein said solvent is selected from the group consisting of dimethyl ether of polyethylene glycol, dimethyl ether of polypropylene glycol, dimethyl ether of tetramethylene glycol, and mixtures thereof.

13. The improvement in the process of claim 12, wherein said solvent is a dimethyl ether of polyethylene glycol containing 3-10 ethylene units and having a molecular weight of 146 to 476.

14. The improvement in the process of any one of claims 10-13, wherein said regenerating is done by distillation.

15. The improvement in the process of claim 14, wherein said regenerating is done by supplying heat to a reboiler to produce an overhead vaporous stream containing water which is cooled, settled, pumped, and returned to said regenerating as reflux after disposing of excess waste water therefrom.

16. The improvement in the process of claim 10, wherein said flashed solvent flow rate ranges between 0.005 and 0.5 gallon per standard cubic foot of said inlet natural gas stream.

17. The improvement in the process of claim 10, wherein said stripping pressure is varied between 50 psia and 450 psia to reject said selected components of said hydrocarbon liquid.

18. The improvement in the process of claim 17, wherein said bottoms temperature of said stripping is varied between 0° F. and 300° F.

19. The improvement in the process of claim 18, wherein said process is operated to remove $C_2+$ hydrocarbon liquids from said inlet natural gas stream and to reject the methane therein as said selected degree.

20. The improved process of claim 10, wherein said flashed solvent stream from said atmospheric pressure stage is flashed at below atmospheric pressure to produce said $C_5+$ hydrocarbons as flashed gases which are sent to said stripping of said step (g) of claim 9 and a selectively lean-and-wet solvent stream for said dividing of said step A.

21. The improved process of claim 20, wherein the pressure in said below-atmospheric pressure stage is selected in order to minimize total energy consumption of said improved process, by balancing the amount of said minor solvent stream and the energy required for said regenerating thereof according to said step B against the energy required for maintaining the pressure in said below-atmospheric pressure stage.

22. A minimal-energy process for removal of $C_2+$ hydrocarbons from a stream of physical solvent, after using said solvent stream for continuously extracting a liquid hydrocarbon product of a selected composition, which is selectively adjustable to substantially any selected degree in accordance with market conditions, from an inlet natural gas stream containing at least 0.2 mol % or volume % of $C_5+$ hydrocarbons and while producing a residue natural gas stream of pipeline quality that selectively includes ethane ($C_2$), propane ($C_3$), and/or butanes ($C_4$), said minimal-energy removal process having the following characteristics:

(a) minimal use of energy in removing $C_5+$ hydrocarbons from said solvent without heating and cooling all of said solvent and (b) simultaneous extraction of said $C_5+$ hydrocarbons to a maximum degree along with $C_2+$ hydrocarbons from said natural gas stream with said physical solvent and then separation of the extracted $C_5+$ hydrocarbons from said solvent, with or without use of subatmospheric pressure flashing, said process comprising:

minimizing the energy required for said process while recovering up to 100% of said $C_5+$ hydrocarbons in accordance with said market conditions by the following steps:

A. selectively extracting said inlet natural gas stream in a first extraction stage with a major solvent stream, which is at a selected solvent flow rate per standard cubic foot of said gas stream, and in a second extraction stage with a regenerated minor solvent stream, said major solvent stream containing up to an equilibrium amount of $C_5+$ hydrocarbons and said regenerated minor solvent stream being lean with respect to $C_1+$ hydrocarbons, whereby said rich solvent stream and said residue natural gas stream are produced, said residue natural gas stream containing selected maximum amounts of $C_2+$ hydrocarbons in accordance with said market conditions;

B. selectively flashing said rich solvent stream to produce at least one $C_1+$ gas fraction and said solvent stream;

C. dividing said solvent stream into a major solvent stream and a slipstream; and D. regenerating said slipstream to produce said regenerated minor solvent stream for said second extraction stage of said step A, while recycling the remainder of said solvent stream to said first extraction stage of said step A, as said major solvent stream.

* * * * *

UNITED STATES PATENT AND TRADEMARK OFFICE
CERTIFICATE OF CORRECTION

PATENT NO. : 4,578,094

DATED : March 25, 1986

INVENTOR(S) : Yuv R. Mehra

Page 1 of 2

It is certified that error appears in the above-identified patent and that said Letters Patent is hereby corrected as shown below:

In the Title Page:

[73] Assignee: El Paso Hydrocarbons Company, Odessa, Tex.

In the Specification:

Column 1, line 19, change "Frpm" to --From--.

Column 10, line 4, change "lean and dry" to --lean-and-dry--.

Column 14, line 28, change "hydrocrbons" to --hydrocarbons--.

In the Claims:

Column 13, line 5, change ":" to --.-- at the end of claim 6.

Column 13, delete lines 6-29, inclusive, between claims 6 and 7.

UNITED STATES PATENT AND TRADEMARK OFFICE
CERTIFICATE OF CORRECTION

PATENT NO. : 4,578,094

DATED : March 25, 1986

INVENTOR(S) : Yuv R. Mehra

It is certified that error appears in the above-identified patent and that said Letters Patent is hereby corrected as shown below:

Column 15, line 22, chang "9" to --8--.

Signed and Sealed this

Nineteenth Day of August 1986

[SEAL]

Attest:

DONALD J. QUIGG

*Attesting Officer*     *Commissioner of Patents and Trademarks*